(12) United States Patent
Kobuke et al.

(10) Patent No.: US 6,429,310 B2
(45) Date of Patent: Aug. 6, 2002

(54) POLY(PORPHYRIN) ARRAYS HAVING MESO-DIMERIC IMIDAZOLYL PORPHYRIN METAL COMPLEXES AS MONOMER UNITS

(75) Inventors: Yoshiaki Kobuke; Kazuya Ogawa; Shin-ichi Kugimiya, all of Ikoma (JP)

(73) Assignee: Nara Institute of Science and Technology, Ikoma (JP)

( * ) Notice: Subject to any disclaimer, the term of this patent is extended or adjusted under 35 U.S.C. 154(b) by 0 days.

(21) Appl. No.: 09/767,900

(22) Filed: Jan. 24, 2001

(30) Foreign Application Priority Data

Jan. 28, 2000 (JP) ........................................ 2000-020133

(51) Int. Cl.$^7$ ............................................ C07D 487/22
(52) U.S. Cl. ........................................................ 540/145
(58) Field of Search ......................................... 540/145

(56) References Cited

PUBLICATIONS

Richard A. Haycock et al, "Self–Assembly of Oligomeric Porphyrin Rings", American Chemical Society, 10.1021/o1000129d (Abstract).
Ulrike Michelsen et al, "Self–Assembled Porphyrin Polymers", Angew. Chem. Int. Ed. 2000, 39, No. 4.
Yoshiaki Kobuke, et al.; "Supramolecular Organization of Imidazolyl–Porphyrin to a Slipped Cofacial Dimer"; J. Am. Chem. Soc., 1994, 116; pp. 4111–4112.
Richard W. Wagner, et al.; "Molecular Optoelectronic Gates"; J. Am. Chem. Soc. 1996, 118, pp. 3996–3997.
Laurent Ruhlmann, et al.; "A Polycationic Zinc–5, 15–Dichlorooctaethylporphyrinate–Viologen Wire"; J. Am. Chem. Soc. 1999, 121, pp. 6664–6667.
Yoshiaki Kobuke, et al.; "Supramolecular Stacks of Bis(Imidazolyl) Porphyrin Through Metal Coordination"; Bull Chem. Soc. Jpn.,1996, 69, pp. 3563–3569.
Kazuya Ogawa, et al.; "Formation of a Giant Supramolecular Porphyrin Array by Self–Coordination";Angew. Chem. Int. Ed. 2000, 39, No. 22, pp. 4070–4073. (7 pages).
Kazuya Ogawa, et al.; "Poly(Porphyring) Linked By Imidazole–Zinc Coordination Bond"; Crest and Nara Institute of Science and Technology; Art. No. 10117, pp 707, 2000.
Yoshiaki Kobuke; "Self–Organization of Porphyrins by Use of Metal Coordination Bonds"; Graduate School of Materials Science, Nara Institute of Science and Technology and Crest.; Article 25204, pp 1466, 2000.

Primary Examiner—Richard L. Raymond
Assistant Examiner—Kahsay Habte
(74) Attorney, Agent, or Firm—Oblon, Spivak, McClelland, Maier & Neustadt, P.C.

(57) ABSTRACT

A poly(porphyrin) represented by a general formula (I) below, which is useful as a molecular wire conducting photonic and electronic energy:

where M is a metal ion selected from the group consisting of Zn, Ga, Ru, Fe and Co, $R_1$ is a group selected from the group consisting of alkyl group, unsubstituted aryl group, alkyl-substituted aryl group, and alkyloxy-substituted aryl group, Im is represented by the following formula:

$Im_1$      $Im_2$ where $R_2$ denotes a hydrogen atom or a methyl group, and n is an integer of 1 or more, provided that the central metal ion represented by M may be coordinated or not coordinated to at least one of the porphyrin rings positioned at both ends of the general formula (I).

17 Claims, 3 Drawing Sheets

POLY(PORPHYRIN) ARRAYS HAVING MESO-DIMERIC IMIDAZOLYL PORPHYRIN METAL COMPLEXES AS MONOMER UNITS

CROSS-REFERENCE TO RELATED APPLICATIONS

This application is based upon and claims the benefit of priority from the prior Japanese Patent Application No. 2000-020133, filed Jan. 28, 2000, the entire contents of which are incorporated herein by reference.

BACKGROUND OF THE INVENTION

The present invention relates to a novel poly(porphyrin) and a method of producing the same. The poly(porphyrin) of the present invention may be used as a device for conducting photonic energy and electronic energy.

It has been expected that porphyrin is used as a device for conducting photonic energy and electronic energy by using a conjugated π electron system. For example, Lindsey et al. have reported a porphyrin polymer (J. Am. Chem. Soc., 118, 3996 (1996)) in which porphyrin units are formed into an array by connecting with a covalent bond. Fuhrhop et al. have reported a linear polymer synthesis (degree of polymerization: 200) by polymerizing porphyrin metal complex units through an electrolytic polymerization reaction (J. Am Chem. Soc., 121, 6664 (1999)).

However, these poly(porphyrin)s are produced by connecting porphyrin monomers with covalent bonds. Once porphyrin units are formed into a poly(porphyrin) array through the covalent bonds, it becomes difficult to flexibly make up and break down the array. Therefore, the application range of the poly(porphyrin) as a photonic or electronic energy-conducting device may be limited.

BRIEF SUMMARY OF THE INVENTION

An object of the present invention is to provide a poly(porphyrin) constructed by porphyrin units, which is easily cleaved or reconstructed, and also provide a method of producing the poly(porphyrin).

The present inventors found that, the coordinate bonds of an imidazolyl porphyrin metal complex dimer, which is formed between a core metal of one monomer to an imidazolyl group of the other monomer are easily cleaved in the presence of a polar solvent such as methanol, even though the binding force of the coordinate bond is quite strong. The present invention was accomplished based on the finding.

The present invention provides a poly(porphyrin) constructed by imidazolyl porphyrin metal complex units, and is represented by the following general formula (I):

where M is a metal ion selected from the group consisting of Zn, Ga, Ru, Fe and Co; $R_1$ is a group selected from the group consisting of an alkyl group, unsubstituted aryl group, alkyl-substituted aryl group, and alkyloxy-substituted aryl group; Im is an imidazolyl group represented by $Im_1$ or $Im_2$ set forth below:

$Im_1$    $Im_2$ where $R_2$ represents a hydrogen atom or a methyl group; and n is an integer of 1 or more; provided that the central metal ion represented by M may be coordinated or not coordinated to at least one of the porphyrin rings positioned at both ends of the general formula (I).

More specifically, in the general formula (I), the alkyl group represented by $R_1$ is an alkyl group having 1–20 carbon atoms. The unsubstituted aryl group represented by $R_1$ is an aryl group having 6–14 carbon atoms. The alkyl-substituted aryl group represented by $R_1$ is an aryl group having 6–14 carbon atoms with at least one alkyl group having 1–18 carbon atoms as a substituent(s). The alkyloxy-substituted aryl group represented by $R_1$ is an aryl group having 6–14 carbon atoms with at least one alkyloxy group having 1–18 carbon atoms as a substituent(s).

Much more specifically, the present invention provides a poly(porphyrin) represented by the formula (I), where M is a zinc ion, $R_1$ is an alkyl group, and Im is $Im_1$ where $R_2$ is a methyl group.

The present invention also provides a method of producing a poly(porphyrin) represented by the general formula (I) mentioned above. The method comprises the steps of:

(a) inserting the metal ion represented by M into a porphyrin monomer represented by a general formula (I) set forth below, as a central metal ion, thereby producing a complementarily coordinated dimer represented by a general formula (III) set forth below:

where M, $R_1$, and Im are as defined above in the general formula (I);

(b) performing a coupling reaction at meso-position of the complementary coordinated dimer of the general formula (III) obtained in the step (a) and removing the central metal ion from them, thereby producing a meso-meso dimer represented by a general formula (IV):

where $R_1$ and Im are as defined above in the general formula (I); and (c) inserting a central metal ion represented by M into the meso-meso dimer of the general formula (IV) obtained in the step (b), thereby coordinating the central metal ion M to Im to produce the poly(porphyrin) represented by the general formula (I).

More specifically, the above step (c) is performed in a solvent where the polarity thereof is controlled.

The present invention is also directed to the step (c) mentioned above, i.e., the present invention provides a method of producing a poly(porphyrin) represented by the general formula (I), comprising a step of inserting the metal ion M into the meso-meso dimer represented by the general formula (IV) in a solvent where the polarity thereof is controlled, wherein $R_1$, Im, $R_2$ and n are as defined above for the general formula (I).

In one aspect of the method of producing a poly(porphyrin) represented by the general formula (I) from the meso-meso dimer represented by general formula (IV), when a mole ratio of the metal ion M to the meso-meso dimer is set at a value less than 2, the thus produced poly(porphyrin) does not have the metal ion represented by M in the porphyrin rings at both ends thereof.

The present invention also provides a method of producing a poly(porphyrin) represented by the general formula (I), comprising a step of adding a predetermined amount of a polar solvent into a solvent of a poly(porphyrin) represented by the general formula (I). The thus produced poly(porphyrin) has the metal ions represented by M in the porphyrin rings at both ends thereof. The number represented by n of the thus produced poly(porphyrin) becomes smaller than that of the starting poly(porphyrin).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Now, the poly(porphyrin) of the present invention represented by a general formula (I) will be explained in detail.

In the general formula (I), M denotes a metal ion to be employed as a central metal ion of the porphyrin. Any metal atom may be employed as the metal ion M as long as it can be coordinated to the nitrogen atom of the imidazolyl group represented by Im. Specific examples of the central metal ion represented by M include Zn, Ga, Ru, Fe and Co. Of them, Zn is preferable in view of manufacturability.

In the general formula (I), the central metal ion represented by M may not be positioned in at least one of the porphyrin rings positioned at both ends thereof. In other words, in the poly(porphyrin) represented by the general formula (I) of the present invention, three types of the poly(porphyrin): (i) a poly(porphyrin) having the central metal ion M in each of the porphyrin rings positioned at both ends thereof; (ii) a poly(porphyrin) having central metal ion M in either one of the porphyrin rings positioned at both ends thereof; and (iii) a poly(porphyrin) having no central metal ion M in the porphyrin rings positioned at both ends thereof, are included.

In the general formula (I), $R_1$ represents a group selected from the group consisting of an alkyl group, unsubstituted aryl group, alkyl-substituted aryl group and alkyloxy-substituted aryl group.

The alkyl groups represented by $R_1$ include straight chain alkyl groups, branched chain alkyl groups, and alicyclic groups. The number of carbon atoms of the alkyl group is preferably 1 to 20, more preferably 7 to 18. The alkyl group represented by $R_1$ may have a substituent as long as polymerization of the porphyrins is adversely affected.

Specific examples of the alkyl group represented by $R_1$ include n-heptyl, n-nonyl, n-undecyl, and n-tridecyl.

The unsubstituted aryl group represented by $R_1$ may include aryl groups having 6–14 carbon atoms, more preferably, 6–12 carbon atoms. Specific examples are phenyl, naphthyl, and biphenyl.

The aryl moieties of the alkyl-substituted aryl group represented by $R_1$ preferably include aryl groups having 6–14 carbon atoms, more preferably, 6–12 carbon atoms. Specific examples are phenyl, naphthyl, and biphenyl.

Examples of the alkyl group to be substituted on the aryl group of the alkyl-substituted aryl group include straight chain alkyl groups, branched chain alkyl groups, and alicyclic groups. The number of carbon atoms of the alkyl group is preferably 1–18, more preferably 1–12. The number of the alkyl substituent is not particularly limited as long as it is substitution-possible number on the aryl group, and the position thereof is not limited as long as the polymerization of the porphyrins is adversely affected. However, 1 to 3 alkyl groups may be substituted on the o-, m-, and/or p-positions in view of manufacturability and solubility etc. Of them, the substitution of the o-position is preferable since an undesirable side reaction can be suppressed.

Specific examples of the alkyl-substituted aryl group represented by $R_1$ include 4-methylphenyl, 4-octylphenyl, and 2,4,6-trimethylphenyl.

In the alkyloxy-substituted aryl group represented by $R_1$, the aryl group is the same as defined in the case of the alkyl-substituted aryl group.

Examples of the alkyloxy group to be substituted on the aryl group of the alkyloxy-substituted aryl group include straight chain alkyloxy group, branched chain alkyloxy groups, and alicyclicoxy groups. The number of carbon atoms of the alkyloxy group is preferably 1–20, more preferably 1–18. The number of the alkyloxy substituents is not particularly limited as long as it is substitution-possible number on the aryl group, and the position thereof is not limited as long as the polymerization of the porphyrins is adversely affected. However, 1 to 3 alkyloxy groups may be substituted on the o-, m-, and/or p-positions in view of manufacturability and solubility etc. Of them, the substitution of the o-position is preferable since an undesirable side reaction can be prevented.

Specific examples of the alkyloxy-substituted aryl group represented by $R_1$ are 4-methoxyphenyl, 4-octyloxyphenyl, and 4-dodecyloxyphenyl.

In the general formula (I), Im is represented by $Im_1$ or $Im_2$ set forth below:

In the formulas $Im_1$ and $Im_2$, $R_2$ represents a hydrogen atom or an alkyl group. The alkyl group includes a straight chain alkyl group, branched chain alkyl group and alicyclic group, provided that the polymerization of porphyrin is adversely affected. The number of carbon atoms of the alkyl group represented by $R_2$ is not particularly limited as long as polymerization of porphyrin is adversely affected. However, $R_2$ preferably has 1–4 carbon atoms. More preferably, $R_2$ is a methyl group when manufacturability is taken into consideration.

In the general formula (I), n may be appropriately set at an integer of 1 or more depending upon desired uses of the poly(porphyrin) and may not be restricted within a particular range. For example, when the poly(porphyrin) of the present invention is used as a photo-conducting device of a micrometer order, n can be set at up to about 714, based on the calculation under the assumption that the repeating unit has a length of 1.4 nm. If a longer poly(porphyrin) array over the micrometer order is desired, the value n can be further increased to, for example, about 800 to 1000. At present, the present inventors have succeeded in synthesizing poly(porphyrin) having the value n of up to about 400.

The poly(porphyrin) represented by the general formula (I) of the present invention is constructed by dimer units. The dimer unit is formed with two porphyrin monomers, each having an imidazolyl substituent and being connected directly to each other, in such a way that π-orbital planes are arranged in an orthogonal orientation as set forth below (hereinafter this dimer unit is referred to as a "meso-meso dimer"). These meso-meso dimers are formed into an array in such a way that one of the π-planes of one meso-meso dimer faces to one of the planes of another meso-meso dimer.

The stereo structure of the meso-meso dimers is maintained as it is after they are formed into a metal complex polymer represented by the general formula (I) of the present invention.

(IV)

In the poly(porphyrin) of the invention, corresponding substituents (M, $R_1$, and Im) of two monomers constructing the meso-meso dimer may be the same or different to each other. However, they are preferably the same in view of manufacturability and purification. Furthermore, although corresponding substituents (M, $R_1$, and Im) of a plurality of meso-meso dimers constituting the poly(porphyrin) of the present invention may be the same or different to each other, they are preferably the same if in the manufacturability is taken into consideration.

(hereinafter referred to as "intra-dimer distance") is 0.84 nm. The closest distance between the central metal of one meso-meso dimer and the central metal of another meso-meso dimer (hereinafter referred to as "inter-dimer distance") is 0.59 nm, as estimated on the basis of the description of Cerius (Angew. Chem, Int. Ed. Engl. 33, 655–657 (1994)).

The poly(porphyrin) of the invention having the above mentioned "intra-dimer distance" and "inter-dimer distance" is equal to a closely spaced chlorophylls of a natural- As shown in the above formula, the closest distance between central metal ions within the meso-meso dimer unit occurring antenna ring. For example, it is said that the "intra-dimer distance" and the "inter-dimer distance" of B850 derived from *Phodopseudomonas acidophilia* are 0.95 nm and 0.89 nm, respectively. By arranging chlorophylls in such a short distance, a strong mutual excitation interaction of chromophores is induced, and the resulting excitation delocalization on the pigment is the source of ultra-fast excitation dynamics. Based on this phenomenon, it is strongly implied that the poly(porphyrin) of the present invention may realize a photonic and electronic-energy conducting system.

The length of a poly(porphyrin) array of the present invention varies depending upon the synthesis conditions. It is confirmed that if the lengths of poly(porphyrin) array fall within the range of 110 to 550 nm, they can be synthesized. However, even if the poly(porphyrin) array do not satisfy the range, the synthesis of the chains is considered possible. Note that the width of the poly(porphyrin) array of the present invention is about 2.5 nm.

In poly(porphyrin) represented by the general formula (I) of the present invention, a coordinate bond between the meso-meso dimers (between a meso-meso dimer and another meso-meso dimer) can be cleaved and reconstructed depending upon the polarity of a solvent. In other words, the coordinate bonds between the meso-meso dimers are in an equilibrium state between a binding state and an dissociating state which can shift from each other depending upon the polarity of a solvent in which the poly(porphyrin) is present. To explain more specifically, the equilibrium shifts toward the binding state in a solvent having low polarity, so that the meso-meso dimers are polymerized (polymerization state), i.e., n in formula (I) increases. In contrast, the equilibrium shifts toward the dissociating state in a solvent having high polarity, thereby the polymer is dissociated into meso-meso dimers (meso-dimer state), i.e., n in formula (I) decreases.

The degree of the polarity of the solvent can be set at an arbitral value depending on a desired degree of polymerization. One of ordinary skill in the art can set the degree of the polarity of the solvent depending on many factors including the chemical structure of the porphyrin ring including substituents that attach to the porphyrin ring, such as $R_1$ and Im, chemical structure of the solvent and the concentration thereof.

Examples of the polar solvents for shifting the equilibrium toward the dissociation state into meso-meso dimers are methanol, ethanol, and pyridine, however, the polar solvent is not limited to these. On the other hand, examples of the solvents that are capable of shifting the equilibrium toward the polymerization state are nonpolar solvents such as chloroform, benzene, and toluene, however the nonpolar solvent is not limited to these.

The dissociation/reconstructing of the coordination bonds between the meso-meso dimers of the poly(porphyrin) can be checked by a change in peak position of an absorption spectrum and fluorescence spectra of a Soret band intrinsic to each of the poly(porphyrin) and the porphyrin dimer.

Now, the method of manufacturing poly(porphyrin) represented by the general formula (I) of the present invention will be explained.

The poly(porphyrin) represented by the general formula (I) can be manufactured by the following steps (a)–(c).

(a) inserting a metal ion M into a porphyrin monomer represented by a general formula (II), as a central metal ion, thereby producing a complementarily coordinated dimer represented by a general formula (III):

where M, $R_1$ and Im are as defined above in the general formula (I);

(b) performing a coupling reaction at meso-position of the complementary coordinated dimer of the general formula (III) obtained in the steps (a) and removing the central metal ion from the thus coupled dimer, thereby producing a meso-meso dimer represented by a general formula (IV):

where, $R_1$ and Im are as defined above in the general formula (I); and (c) inserting a central metal ion M into the meso-meso dimer represented by the general formula (IV) obtained in the step (b) to coordinate the central metal ion M to Im, thereby producing the poly(porphyrin) represented by the general formula (I).

Now, the method of producing the poly(porphyrin) represented by the general formula (I) of the present invention will be explained by referring to a poly(porphyrin), wherein $R_1$=n-$C_7H_{15}$, M=Zn, and Im=$Im_1$ ($R_2$=methyl group) as an example. However, the method of producing the poly (porphyrin) of the present invention is not limited to this example. In addition, it is possible for one of ordinary skill in the art to produce other poly(porphyrin) within the scope of the invention by appropriately varying a compound(s) to be used and reaction conditions such as a catalyst and a reaction temperature.

The starting material of the step (a), that is, a porphyrin monomer represented by a general formula (II) is obtained by dissolving 1-methylimidazole-2-carboxyaldehyde, formaldehyde, and meso-(n-heptyl)dipyrromethane in a nonpolar solvent, stirring the mixture, and thereafter, adding trifluoroacetic acid and dichlorodicyano-p-benzoquinone to the resultant mixture.

In the aforementioned reaction, 1-methylimidazole-2-carboxyaldehyde and formaldehyde are commercially available. Meso-(n-heptyl) dipyrromethane may be produced from octanal and pyrrole in accordance with a method described in technical literatures.

A mole ratio of 1-methylimidazole-2-carboxyaldehyde: formaldehyde: meso-(n-heptyl)dipyrromethane generally falls within the range of 1:4:2 to 1:3:2.

As the nonpolar solvent, chloroform, THF or the like may be used. Generally, the nonpolar solvent is used in an amount that is 500–1000 times the weight of chemical compounds to be reacted.

The amount of trifluoroacetic acid to be added to the reaction solution is generally 1 to 3 times that of 1-methylimidazole-2-carboxyaldehyde, in terms of mole. This reaction of these compounds are generally performed at a temperature near room temperature under an inert gas atmosphere such as nitrogen while stirring for 20 to 40 minutes.

The amount of dichlorodicyano-p-benzoquinone to be added to the reaction solution after stirring is 2 to 4 times that of 1-methylimidazole-2-carboxyaldehyde, in terms of mole. This reaction is generally performed with stirring for 30 minutes to one hour.

The resultant reaction solution is washed with an aqueous solvent such as aqueous sodium bicarbonate, and thereafter, an organic layer is evaporated. In this manner, a crude product represented by the general formula (II) can be obtained. The crude product is, if necessary, purified by means of column chromatography or the like, and then used as the starting material of the step (a).

In the step (a), the porphyrin monomer represented by the general formula (II) is dissolved in a nonpolar solvent and a solution containing a zinc salt dissolved in an organic solvent is added to the above-prepared solution. In this manner, a complementarily coordinated dimer represented by the general formula (III) can be obtained.

As an example of the nonpolar solvent for dissolving the porphyrin monomer of the general formula (II), chloroform, or dichloromethane may be used. Generally, the amount of the nonpolar solvent may be 100 to 200 times of the weight of the compound to be dissolved.

As the solution prepared by dissolving a zinc salt in an organic solvent, a solution prepared by dissolving, zinc acetate, zinc chloride, or the like in an organic solvent such as methanol or ethanol may be used. The molar amount of the zinc salt is 5 to 20 times that of the monomer represented by the general formula (II) in terms of zinc.

The reaction mixture is generally stirred for 1 to 3 hours at around room temperature. After the resultant reaction solution is washed with an aqueous solvent such as water, the organic layer is removed by evaporation. As a result, a crude product of the complementarily coordinated dimer represented by the general formula (III) can be obtained.

In the step (b), the complementarily coordinated dimer represented by the general formula (III) and iodine are dissolved in a nonpolar solvent. After silver(I) hexafluorophosphate dissolved in an organic solvent is added and stirred, iodine and silver(I)hexafluorophosphate are further added to the reaction mixture and stirred, thereby the dimers are polymerized.

Then, the reaction solution is washed with an aqueous solvent to eliminate the solvent. Subsequently, the residue is dissolved in an acid-containing organic solvent and stirred, thereby the central metals are removed. After an aqueous solvent is added, the resultant solution mixture is subjected to extraction with an organic solvent. As a result, a crude product of the meso-meso dimer represented by the general formula (IV) is obtained.

As the nonpolar solvent for dissolving the complementarily coordinated dimer represented by the general formula (III), chloroform or the like is used. Chloroform may be used in an amount which is 500 to 1000 times the weight of the chemical compound to be reacted. Iodine and silver(I) hexafluorophosphate may be added in an amount 0.4 to 0.6 times that of the dimer represented by the general formula (III) in terms of mole, for each.

As an example of the organic solvent for dissolving silver(I)hexafluorophosphate, acetonitrile, or acetone may be added in an amount 100 to 200 times the weight of silver(I)hexafluorophosphate.

The stirring is generally performed at room temperature for 1 to 3 hours.

The amounts of iodine and silver(I)hexafluorophosphate to be further added are 0.4 to 0.6 times that of the dimer of the general formula (III), for each. The reaction solution is generally stirred for 1 to 3 hours.

As an example of the aqueous solvent for washing the reaction solution, an aqueous sodium bicarbonate solution, or water may be used.

As the acid-containing organic solvent for dissolving the residue after washing, any organic solvent may be used as long as it can reduce a pH value of the reaction mixture to 1 or less. For example, methanol/conc. hydrochloric acid (10:1) mixture may be used in an amount 200 to 500 times the weight of the chemical compounds to be reacted in the coupling reaction. The reaction solution is generally stirred at room temperature for 20 to 40 minutes.

As an example of the aqueous solvent to be added to the resultant reaction solution, water may be used. As an example of the organic solvent for use in extraction, chloroform may be used.

The crude product of the meso-meso dimer of the general formula (IV) thus obtained, if necessary, is washed with an aqueous solvent such as aqueous sodium bicarbonate or water, and purified by chromatography or the like and thereafter, subjected to the next step (c).

In the step (c), the meso-meso dimer of the general formula (IV) is dissolved in a solvent having low polarity. To the resultant solution, a zinc salt dissolved in an organic solvent is added and stirred. As a result, the poly(porphyrin) represented by the general formula (I) of the present invention can be obtained.

As mentioned above, the degree of polymerization varies depending on the polarity of the solvent that is used in the steps (c). One of ordinary skill in the art can set the degree of the polarity of the solvent depending on many facters including the chemical structure of the porphyrin ring including substituents that attach to the porphyrin ring, such as $R_1$ and Im, chemical structure of the solvent and the concentration thereof. When the reaction in the step (c) is performed in a solvent free from a polar solvent, i.e., in a non polar solvent, the degree of polymerization can reach maximum.

As an example of the nonpolar solvent to be used in the reaction of the step (c), chloroform, or dichloromethane may be used. The nonpolar solvent may be used in an amount that is 100 to 200 times the weight of the compound.

As the solution having a zinc salt dissolved in an organic solvent and to be added to the reaction mixture, use is made, for example, of a saturated solution containing zinc acetate, or zinc chloride dissolved in an organic solvent such as methanol or ethanol. The molar amount of the zinc salt may be 5 to 20 times that of the meso-meso dimer of the general formula (IV) in terms of zinc.

The reaction is generally performed at room temperature for 1 to 3 hours with stirring, thereby poly(porphyrin) represented by the general formula (I) of the present invention can be obtained.

In the reaction of the step (c), a product can be obtained in a yield of almost 100%. Therefore, the value n in the general formula (I) of the present invention can be set at a desired value by adjusting the amount of the meso-meso dimer on the basis of that of zinc to be used in the step (c).

The obtained reaction solution is washed with an aqueous solvent such as water and then the solvent is removed by evaporation, thereby the poly(porphyrin) is purified.

During the preparation of the poly(porphyrin) of the general formula (I) of the present invention, if the reaction condition is appropriately set, the resultant poly(porphyrin) can be obtained with a desired degree of polymerization (n in formula (I)). Further, the presence and absence of metal ion M to be coordinated to at least one of the porphyrin ring located at both ends can be controlled by setting the reaction conditions.

It is also possible to control the degree of polymerization after the poly(porphyrin) of the present invention is once polymerized. Specifically, poly(porphyrin) is dissolved in, for example, a nonpolar solvent, and add a polar organic solvent appropriately to the mixture. More specifically, the value n of the poly(porphyrin) of the general formula (I) can be freely changed from 1 to about 400 or more by varying the polarity of the solvent. The polarity of the solvent can be set by varying the amount of the polar solvent to be added. As an example of the nonpolar solvent to be used in this reaction, chloroform, benzene, or toluene may be used. As an example of the polar organic solvent, methanol, or ethanol may be used. The amount of the polar organic solvent to be added may be 0–30 on the basis of the volume of the nonpolar solvent being 100. The reaction is generally performed at room temperature for several minutes with stirring.

Poly(porphyrin) obtained by the aforementioned method has metal ions M's in the porphyrin rings positioned on both ends thereof.

On the other hand, it is also possible to control the degree of polymerization of poly(porphyrin) of the present invention during its synthesis process. Specifically, when the number of moles of the central metal ion to be coordinated, on the basis of the number of moles of the meso-meso dimer of the general formula (IV), is appropriately set, the polymerization degree can be controlled. More specifically, the meso-meso dimer of the general formula (IV) is dissolved in a nonpolar solvent and a salt of the metal ion dissolved in an organic solvent is added and stirred. As the nonpolar solvent to be used in the reaction, chloroform, dichloromethane or the like may be used in an amount of 100 to 200 times the weight of the compounds to be reacted.

As an example of the salt of the metal ion to be added, an acetate or a chloride of the metal ion M defined in the general formula (I), may be used. As an example of the organic solvent for dissolving the salt of the metal ion M, methanol, or ethanol may be used.

If the molar amount of the metal ion to be coordinated is set twice the number of moles of the meso-meso dimer to be polymerized, the degree of polymerization is determined depending upon the number of moles of the meso-meso dimer. In this case, the obtained poly(porphyrin) has metal ions M's coordinated in the porphyrin rings positioned on both ends thereof.

On the other hand, if the molar amount of the metal ion to be added is less than two times, for example, 1 to 1.5 times, that of the meso-meso dimer to be polymerized, the metal ion M is not coordinated at the porphyrin rings positioned at both ends in the obtained poly(porphyrin). In addition, the degree of polymerization of the thus obtained poly(porphyrin) is smaller than that obtained in the case where all possible meso-meso dimers are polymerized.

Furthermore, in the poly(porphyrin) of the general formula (I) having the central metal ion M in only one of the porphyrin rings positioned at both ends thereof, the degree of polymerization can be adjusted as follows. First, the meso-meso dimer represented by the general formula (IV) is synthesized so as to coordinate the central metal ion in one of the porphyrin rings. Then, the poly(porphyrin) represented by the general formula (I) of the present invention having a desired degree of polymerization and having the central metal ions coordinated at the porphyrin rings positioned at both ends is added to the meso-meso dimer of the general formula (IV).

EXAMPLES

Examples of the present invention will be explained below. However, the present invention will not be limited to these examples.

The poly(porphyrin) of the present invention was prepared by the following method.

Synthesis Example 1

1

-continued

1) Synthesis of 5-(1-methyl-2-imidazolyl)-10,20-bis(n-heptyl)porphyrin (1)

Under a nitrogen atmospheres, 1-methylimidazol-2-carboxyaldehyde (4 mmol), formaldehyde (16 mmol) and meso-(n-heptyl)dipyrromethane (8 mmol) were dissolved in 400 mL of chloroform and trifluoroacetic acid (8 mmol) was added to the mixture. After stirring for 30 minutes at room temperature, dichlorodicyano-p-benzoquinone (12 mmol) was added, and the reaction mixture was stirred for a further one hour. The reaction solution was washed with aqueous sodium bicarbonate, and then an organic layer was evaporated. The crude product was purified by silica gel column chromatography (eluent: chloroform/acetone=10:1), to obtain 0.11 mmol (yield 2.8%) of the above-title substance 1.

Mass spectrometry (MALDI-TOF) found for [M+H]$^+$: 587.2, calculated: 587.31; λabs (chloroform) 414, 512, 554, 588, 643 nm; $^1$H NMR(270 MHz, CDCl$_3$) δ10.12(s,15,1H), 9.50(d,J=4.9 Hz,3,7,2H), 9.42(d,J=4.9 Hz,12,1.8,2H), 9.35 (d,J=4.6 Hz,2,8,2H), 8.73(d,J=4.6 Hz,13,17,2H), 7.69(im-5, s,1H), 7.47(im-4,s,1H), 4.91(t,J=7.8 Hz,CH$_2$), 3.35(s,CH$_3$(im),3H), 2.49(quintet,J=7.3 Hz,CH$_2$), 1.77(quintet,J=7.3 Hz,CH$_2$), 1.50(quintet,J=7.3 Hz,CH$_2$), 1.32(m,CH$_2$), 0.89(t,J=7.3 Hz,CH$_3$), −2.95(s,NH,2H).

2) Synthesis of bis [5-(1-methyl-2-imidazolyl)-10,20-bis(n-heptyl)porpyrinatozinc (II) (2)

To a solution of the above-title substance 1 (0.20 mmol) in 10 mL of chloroform was added 3 ml of a saturated solution of zinc acetate dihydrate in methanol. After stirring for 2 hours at room temperature, the reaction solution was washed with water and evaporated, to obtain the above-title substance 2 (0.18 mmol, yield 88%).

Mass spectrometry (MALDI-TOF) found for [M+H]$^+$: 649.29, calculated: 649.18, found for [2M+H]$^+$: 1297.0, calculated: 1297.58; λabs (chloroform) 414, 512, 554, 588, 643 nm.

3) Synthesis of 15,15'-bis(1-methyl-2-imidazolyl)-10,10',20,20'-tetrakis-(n-heptyl)5,5'-bisporphyrin (3)

The aforementioned substance 2 (0.067 mmol) and iodine (0.0335 mmol) were dissolved in 25 mL of chloroform, and a solution of silver(I)hexafluorophosphate (0.0335 mmol) in 1 mL of acetonitrile was added. After stirring for 2 hours at room temperature, iodine (0.0335 mmol) and silver(I) hexafluorophosphate (0.0335 mmol) were added and the reaction mixture was stirred for further two hours. The reaction solution was washed with aqueous sodium bicarbonate and then rinsed with water. The solvent was removed by evaporation. The residue was dissolved in 11 mL of methanol/conc. hydrochloric acid (10:1) and stirred for 30 minutes at room temperature. After adding water, the solution was extracted with chloroform, and washed with aqueous sodium bicarbonate and water.

The product was purified by preparative gel permeation chromatography (recycling HPLC system made by Japanese Analytical Industry Co., Ltd. with JA 2H and 2.5H column (60 cm each in series), to obtain 0.012 mmol of the above-title substance 3 (yield 18%). Mass spectrometry (MALDI-TOF) found for [M+H]$^+$:1172.65, calculated: 1172.61; λabs (chloroform) 415, 453, 525, 562, 597, 657 nm; $^1$H NMR(270 MHz, CDCl$_3$) δ9.51 & 9.52(d & d,J=4.6 & 4.6 Hz,3,7,3', 7',4H), 9.09 & 9.15(d & d,J=4.6 & 4.6 Hz,12,18,12',18',4H), 8.89(d,J=4.6 Hz,2,8,2',8',4H), 7.98 & 8.14(d & d,J=4.6 & 4.6 Hz,13,17,13',17',4H), 7.75(s,im-5,2H), 7.53(s,im-4,2H), 4.91(br,CH$_2$,8H), 3.51(s, CH$_3$(im),6H), 2.50(br,CH$_2$,8H), 1.73(br,CH$_2$,8H), 1.45(br,CH$_2$,8H), 1.27(br,CH$_2$,16H), 0.83 (t,J=7.0 Hz,CH$_3$,6H), 0.82(t,J=7.0 Hz,CH$_3$,6H), −2.07(s, NH,4H).

4) Synthesis of [15,15'-bis(1-methyl-2-imidazolyl)-10,10',20,20,'-tetrakis(n-heptyl)5,5'-bisporphyrinatozinc (II)]$_n$ (4)

To a solution of the aforementioned substance 3 (0.012 mmol) in 1 mL of chloroform was added 0.3 mL of a saturated solution of zinc acetate dihydrate in methanol. After stirring for 2 hours at room temperature, the starting material 3 was disappeared completely, as checked by TLC. The solution was washed with water and evaporated to obtain the above-title substance 4 as a dark-brown solid material (0.012 mmol, yield 100%)

λabs (chloroform) 412, 490, 584, 647 nm. .

Synthesis Example 2

Poly(porphyrin) substance 4 ($n<400$) synthesized by the method of Synthesis Example 1 was dissolved in 3 mL of chloroform and 0.3 mL of ethanol was added thereto. The reaction solution was stirred at room temperature for several minutes. As a result, a meso-meso dimer ($n=1$) was obtained.

The meso-meso dimer ($n=1$) was subjected to Measurement Example 4 set forth below.

Synthesis Example 3

Synthesis of 15,15'-bis(1-methyl-2-imidazolyl)-10, 10',20,20'-tetrakis(n-heptyl)-5,5'-bisporphyrinato monozinc complex (5')

-continued

5

$R_1 = n\text{-}C_7H_{15}$

Im = [1-methyl-imidazolyl structure]

The substance 3 (39.49 μmol) obtained in Synthesis Example 1 was dissolved in 1 mL of chloroform, and 14 μL of a saturated solution of zinc acetate in methanol was added to the resultant solution and stirred at room temperature for 2 hours. After UV spectrum or the like was confirmed, the resultant solution was washed with water. An organic layer is concentrated and purified by preparative gel permeation chromatography (recycling HPLC system made by Japanese Analytical Industry Co., Ltd. with JA 2H and 2.5H column (60 cm each in series). As a result, the above-title substance 5' was obtained (4.70 mol, yield 49%). Mass spectrometry (TOF)m/e 1235.68 (M) found: 1232.65 (in terms of substance 5'); UV visible absorption spectrum (CHCl$_3$) λmax 415.5, 468, 521, 575, 625, 662 nm; fluorescence spectra (CHCl$_3$) λmax 680(λext 416 nm).

Note that UV visible absorption spectrum and fluorescence spectra were those of the substance 5 set forth above.

$^1$H NMR(270 MHZ, CDCl$_3$) δ9.65 & 9.61(d & d,J=4.6 & 4.6 Hz,13,17,4H), 9.47 & 9.49(d & d,J=4.6 & 4.6 Hz,3',7',4H), 9.38 & 9.33(d & d,J=4.6 & 4.6 Hz,12', 18',4H), 9.09 & 9.07(d & d,J=4.6 Hz,2,8,4H), 8.98(d, J=4.6 Hz,12,18,2H), 8.87(d,J=4.6 Hz,2',8',4H), 8.33 & 8.15(d & d,J=4.6 & 4.6 Hz,13',17',4H), 7.81(s,im-4', 2H), 7.59(s,im-5',2H), 7.45(d,J=4.6 Hz,12,18,2H), 6.02 (s,im-5,2H), 5.74 & 5.76(d & d, J=4.6 & 4.6 Hz, 3,7,4H),5.14 & 4.82(br,CH$_2$,16H), 3.58(s,CH$_3$(im'), 6H), 2.97,2.75 & 2.44(br,CH$_2$,16H), 1.94(s,CH$_3$(im), 6H), 1.55(br,CH$_2$), 0.94(t,J=6.8 Hz,CH$_3$,24H), −1.94(s, NH,4H).

Measurement Example 1

[15,15'-bis(1-methyl-2-imidazolyl)-10,10',20,20'-tetrakis-(n-heptyl)5,5'-bisporphyrinatozinc (II)]$_n$ (substance 4) obtained above Synthesis Example 1 was measured for the molecular weight by gel permeation chromatography [JA 4HA column (45 cm, exclusion limitation: 5×10$^5$ dalton, Japanese Analytical Industry Co., Ltd.).

Figure 1:
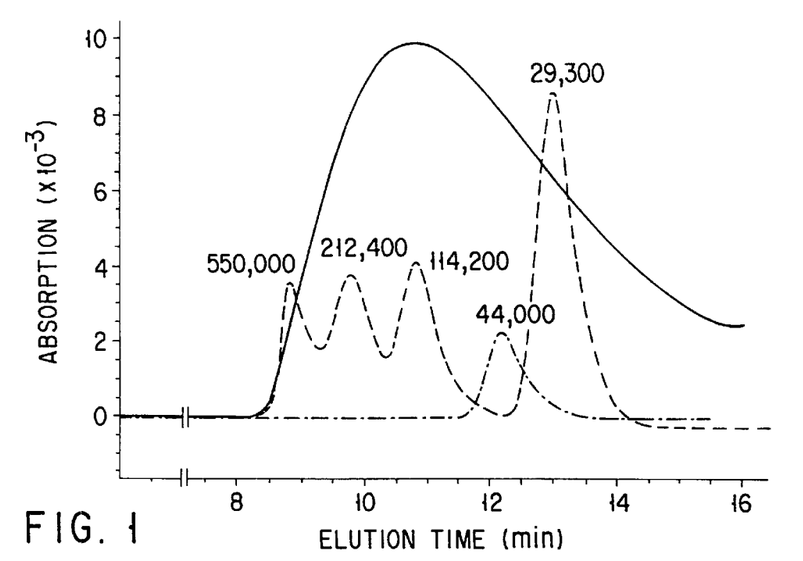
FIG. 1 shows gel permeation column chromatograms for determining the molecular weight of the poly(porphyrin) obtained in Synthesis Example 1.

FIG. 1 shows a chromatogram (solid line) of substance 4 and a chromatogram (broken lines) of polystyrene serving as a reference mixture.

As is apparent from the elution curve of substance 4 shown in FIG. 1, the elution of substance 4 starts earlier than that of the reference substance having a molecular weight of 5.5×10$^5$ and reaches a peak at a molecular weight of 1×10$^5$. The molecular weight of 1×10$^5$ corresponds to a substance having about 80 units of bis(imidazolylporphyrin) (molecular weight 1298) bonded to each other through imidazole-zinc coordination bonds.

According to the molecular mechanics using Cerius (Angew. Chem, Int. Ed. Engl. 33, 655–657(1994)), the molecular length of a repeating unit is estimated at 1.43 nm. Therefore, the array length of poly(porphyrin) of substance 4 is 550 nm at the maximum, with most frequently appearing array length of 110 nm.

Measurement Example 2

A chloroform solution of substance 4 was poured and spread over a mica plate to prepare a cast film. In the cast film, the poly(porphyrin) of the present invention has a length of 30 to 200 nm and a thickness of 0.7 nm.

Figure 2A:
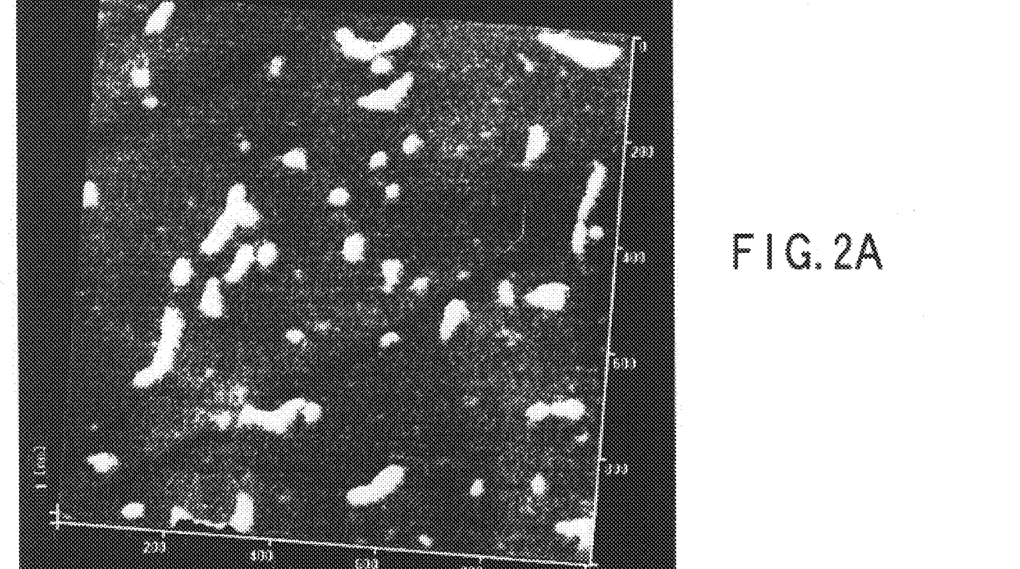
FIG. 2A is a photograph taken with an atomic force microscope showing a cast film of the poly(porphyrin) of the present invention.
Figure 3:
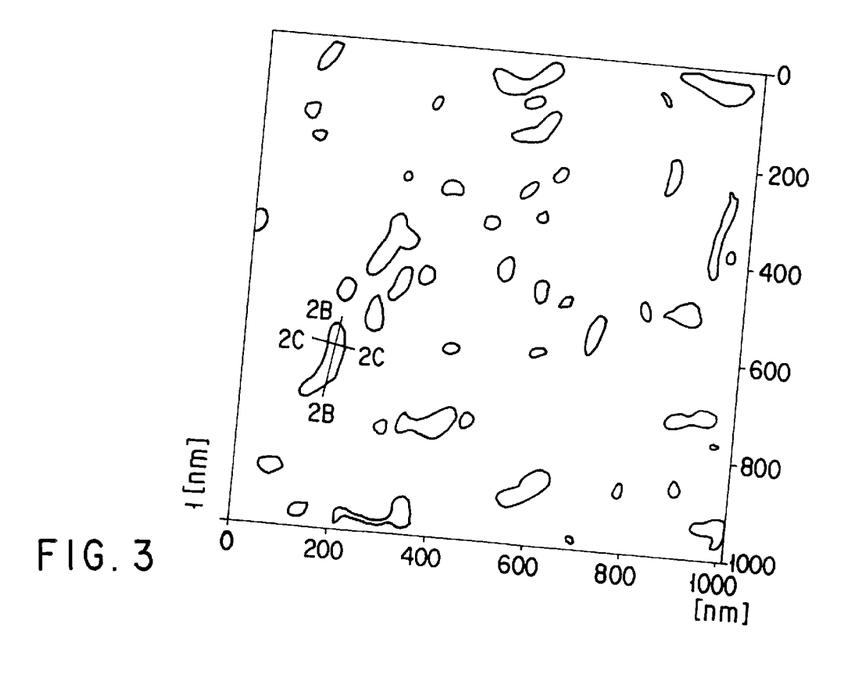
FIG. 3 is a schematic view showing positions of poly(porphyrin) along which the cross-sections of FIGS. 2B and 2C are taken.

Atomic force microscopy of the cast film is set forth in FIG. 2A (scanning probe microscope system SPI3800N having a curvature of 10 nm, manufactured by Seiko Instrument Co., Ltd.). A schematic view of the photomicrograph of FIG. 2A is shown in FIG. 3 to illustrate the positions of the cross lines 2B—2B and 2C—2C.

Figure 2B:
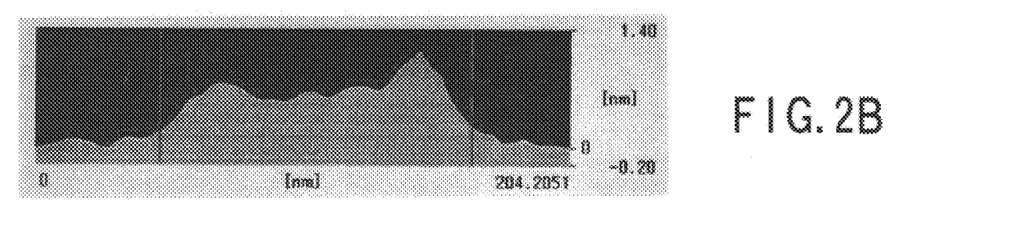
FIG. 2B is a cross-sectional view of 2B—2B line of the poly(porphyrin) of FIG. 2A.
Figure 2C:
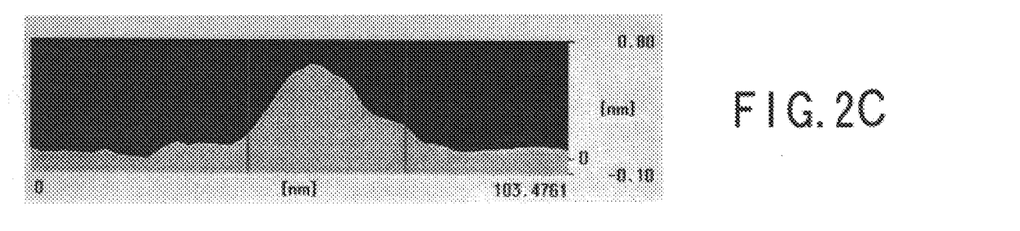
FIG. 2C is a cross-sectional view of 2C—2C line of the poly(porphyrin) of FIG. 2A.

As is apparent from FIG. 2A, the cast film has a wire like structure. The lengths of most of the wires fall within 30 to 200 nm. As the result that typical wire pieces were observed more specifically, the thickness of the molecule was estimated at 0.7 nm (see cross sectional views shown in FIGS. 2B and 2C). From these results, it is concluded that the poly(porphyrin) of the present invention has a structure of a one-dimensionally propagated multi-porphyrin arrays.

Measurement Example 3

The absorption spectrum of substance 4 (obtained in Synthesis Example 1) was determined by UV 3100PC (manufactured by Shimazu Corporation) and compared with the adsorption spectra of a zinc/imidazolyl porphyrin complex (substance 3 obtained in Synthesis Example 1) and free base imidazolyl porphyrin (substance 1 obtained in the Synthesis Example 1). In either case, chloroform was used as a solvent.

Figure 4:
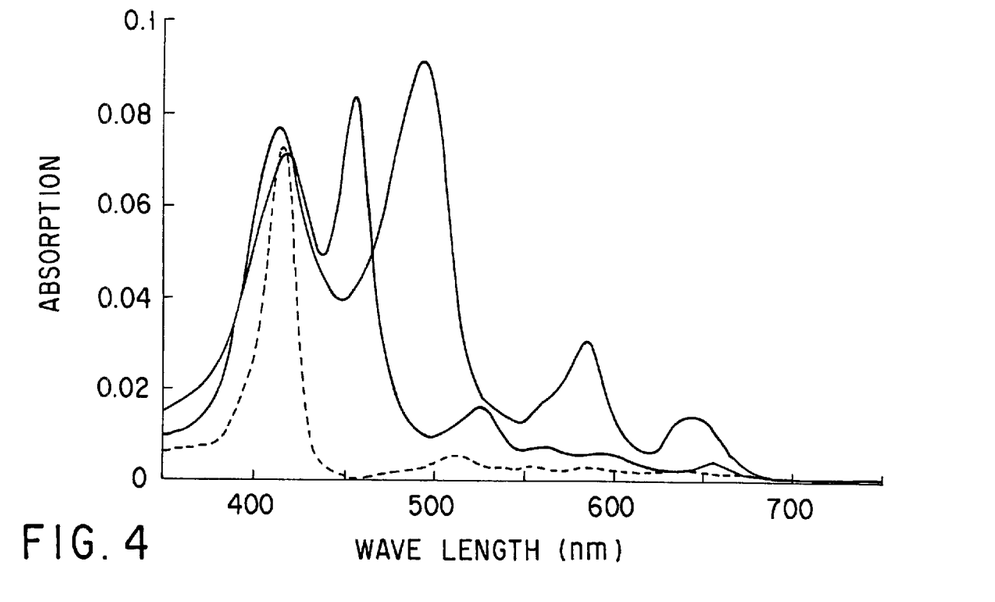
FIG. 4 is an absorption spectrum of the poly(porphyrin) obtained in Synthesis Example 1.

The obtained absorption spectrum is shown in FIG. 4. In FIG. 4, the thick solid line indicates substance 4, the thin solid line indicates substance 3, and the broken line indicates substance 1.

It is clear from FIG. 4 that substance 4 has two peaks at 412 and 490 nm. In contrast, substance 1 has a single peak at 414 nm, and substance 3 has two peaks at 415 and 453 nm.

Measurement Example 4

Effect of a polar solvent upon substance 4 contained in chloroform was checked by an absorption spectrum to investigate the relationship between polarity of the solvent and degree of polymerization.

An absorption spectrum was observed with respect to the cases where ethanol was added in a quantity of 0, 1, 2, 3, 4, 5, 7, 9, 10, 12, 14, 16, 20, 25 and 30 times the volume of chloroform being 100.

Figure 5:
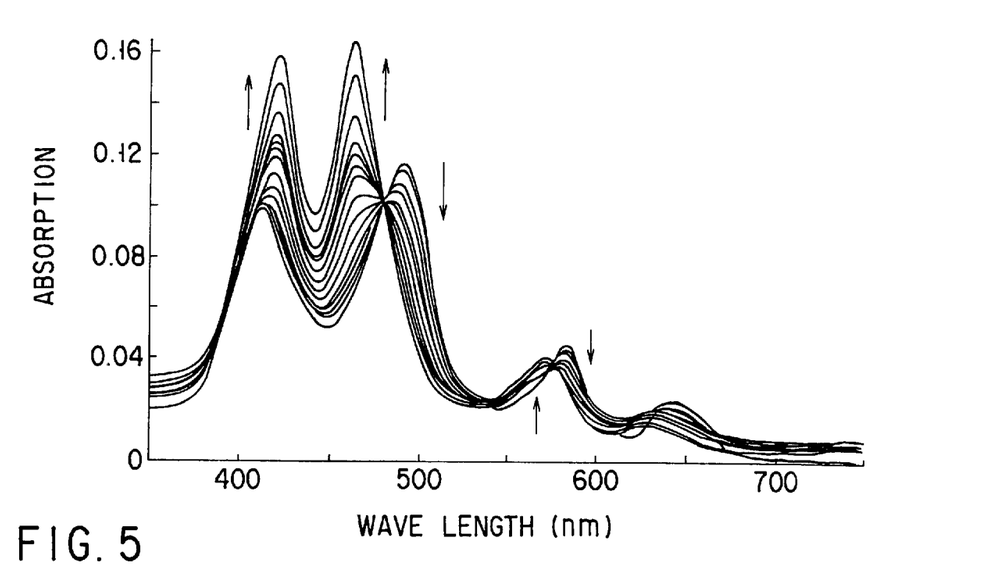
FIG. 5 is an absorption spectrum for checking the effect of a polar solvent upon the poly(porphyrin) of the present invention.

The obtained absorption spectrum was shown in FIG. 5. In FIG. 5, each arrow indicates that the spectra were obtained when the ethanol concentrations were increased in the direction shown by the arrow.

As is apparent from FIG. 5, the widths of two peaks within a Soret band intrinsic to the poly(porphyrin) of the present invention become narrower as the amount of ethanol increases. The peak (490 nm) in the long wavelength side shifts toward a short wave length side by way of an isosbestic point (478 nm). The shift toward the short wavelength side reaches saturation by addition of 30% ethanol. The width of the peak results in 41 nm. The peak width of 41 nm corresponds to the wavelength of substance 3 (meso-meso dimer).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. Poly(porphyrin) represented by the following formula (I):

wherein M is a metal ion selected from the group consisting of ions of Zn, Ga, Ru, Fe and Co; $R_1$ is a group selected from the group consisting of an alkyl group, unsubstituted aryl group, alkyl-substituted aryl group, and alkyloxy-substituted aryl group; Im is an imidazolyl group represented by $Im_1$ or $Im_2$ set forth below:

wherein $R_2$ represents a hydrogen atom or a methyl group; and n is an integer of 1 or more; provided that the central metal ion represented by M may be coordinated or not coordinated to at least one of the porphyrin rings positioned at both ends of the formula (I).

2. The poly(porphyrin) according to claim 1, wherein the alkyl group represented by $R_1$ is an alkyl group having 1–20 carbon atoms; the unsubstituted aryl group is an aryl group having 6–14 carbon atoms; the alkyl-substituted aryl group is an aryl group having 6–14 carbon atoms with at least one alkyl group having 1–18 carbon atoms as a substituent; and the alkyloxy-substituted aryl group is an aryl group having 6–14 carbon atoms with at least one alkyloxy group having 1–18 carbon atoms as a substituent.

3. The poly(porphyrin) according to claim 2, wherein M is a zinc ion; $R_1$ is an alkyl group; and Im is $Im_1$ wherein $R_2$ is a methyl group.

4. A method of producing a poly(porphyrin) represented by the formula (I) of claim 1, comprising the steps of:

(a) inserting the metal ion represented by M, as a central metal ion, into a porphyrin monomer represented by a formula (II) thereby producing a complementarily coordinated dimer represented by a formula (III):

wherein M, $R_1$, and Im are as defined in claim 1;

(b) removing the central metal ion from the complementarily coordinated dimer of the formula (III), thereby producing a meso-meso dimer represented by a formula (IV):

(IV)

wherein $R_1$ and Im are as defined in claim 1; and (c) inserting a central metal ion represented by M into the meso-meso dimer of the formula (IV), thereby coordinating the central metal ion M to Im to produce the poly(porphyrin) represented by the formula (I).

5. The method according to claim 4, wherein the step (c) is performed by decreasing the polarity of the resultant organic layer in which the metal complex of the meso-meso dimer of the general formula (IV) is present.

6. The method according to claim 5, wherein the solvent is free from a polar solvent.

7. The method according to claim 4, wherein the alkyl group represented by $R_1$ is an alkyl group having 1–20 carbon atoms; the unsubstituted aryl group is an aryl group having 6–14 carbon atoms; the alkyl-substituted aryl group is an aryl group having 6–14 carbon atoms with at least one alkyl group having 1–18 carbon atoms as a substituent; and the alkyloxy-substituted aryl group is an aryl group having 6–14 carbon atoms with at least one alkyloxy group having 1–18 carbon atoms as a substituent.

8. The method according to claim 7, wherein M is a zinc ion; $R_1$ is an alkyl group; and Im is $Im_1$ wherein $R_2$ is a methyl group.

9. A method of producing a poly(porphyrin) represented by the formula (I) of claim 1, comprising a step of inserting the metal ion M into a meso-meso dimer represented by the formula (IV),

(IV)

in a solvent free from a polar solvent, wherein $R_1$, M, n, Im, and $R_2$ are as defined in claim 1.

10. The method according to claim 9, wherein the alkyl group represented by $R_1$ is an alkyl group having 1–20 carbon atoms; the unsubstituted aryl group is an aryl group having 6–14 carbon atoms; the alkyl-substituted aryl group is an aryl group having 6–14 carbon atoms with at least one alkyl group having 1–18 carbon atoms as a substituent; and the alkyloxy-substituted aryl group is an aryl group having 6–14 carbon atoms with at least one alkyloxy group having 1–18 carbon atoms as a substituent.

11. The method according to claim 10, wherein M is a zinc ion; $R_1$ is an alkyl group; and Im is $Im_1$ wherein $R_2$ is a methyl group.

12. A method of producing a poly(porphyrin) represented by the formula (I) of claim 1 having no metal ion represented by M in the porphyrin rings at both ends thereof, comprising a step of inserting the metal ion M into a meso-meso dimer represented by the formula (IV), (IV)

in a solvent free from a polar solvent, where a mole ratio of the metal ion M to the meso-meso dimer represented by formula (IV) is set less than 2, wherein $R_1$, M, n, Im, and $R_2$ are as defined in claim 1.

13. The method according to claim 12, wherein the alkyl group represented by $R_1$ is an alkyl group having 1–20 carbon atoms; the unsubstituted aryl group is an aryl group having 6–14 carbon atoms; the alkyl-substituted aryl group is an aryl group having 6–14 carbon atoms with at least one alkyl group having 1–18 carbon atoms as a substituent; and the alkyloxy-substituted aryl group is an aryl group having 6–14 carbon atoms with at least one alkyloxy group having 1–18 carbon atoms as a substituent.

14. The method according to claim 13, wherein M is a zinc ion; $R_1$ is an alkyl group; and Im is $Im_1$ wherein $R_2$ is a methyl group.

15. A method of producing a poly(porphyrin) represented by the formula (I) of claim 1 having a metal ion M in each of the porphyrin rings at both ends thereof, comprising a step of adding a certain amount of a polar solvent into a solvent that is free from a polar solvent and containing a starting poly(porphyrin) represented by the formula (I), thereby producing another poly(porphyrin) represented by the formula (I) having the number represented by n that is smaller than that of the starting poly(porphyrin) represented by the formula (I), wherein $R_1$, M, n, Im, and $R_2$ are as defined in claim 1.

16. The method according to claim 15, wherein the alkyl group represented by $R_1$ is an alkyl group having 1–20 carbon atoms; the unsubstituted aryl group is an aryl group having 6–14 carbon atoms; the alkyl-substituted aryl group is an aryl group having 6–14 carbon atoms with at least one alkyl group having 1–18 carbon atoms as a substituent; and the alkyloxy-substituted aryl group is an aryl group having 6–14 carbon atoms with at least one alkyloxy group having 1–18 carbon atoms as a substituent.

17. The method according to claim 16, wherein M is a zinc ion; $R_1$ is an alkyl group; and Im is $Im_1$ wherein $R_2$ is a methyl group.

* * * * *